United States Patent [19]

Hickey

[11] Patent Number: 4,784,651
[45] Date of Patent: Nov. 15, 1988

[54] URETHRAL CATHETER

[75] Inventor: David S. Hickey, Manchester, England

[73] Assignee: The Victoria University of Manchester, Manchester, England

[21] Appl. No.: 924,841

[22] PCT Filed: Mar. 11, 1986

[86] PCT No.: PCT/EP86/00132
§ 371 Date: Oct. 21, 1986
§ 102(e) Date: Oct. 21, 1986

[87] PCT Pub. No.: WO86/05403
PCT Pub. Date: Sep. 25, 1986

[30] Foreign Application Priority Data

Mar. 14, 1985 [GB] United Kingdom ............... 8506638

[51] Int. Cl.$^4$ ............................................. A61M 25/00
[52] U.S. Cl. ..................................... 604/282; 604/96; 604/230; 604/93; 128/DIG. 25; 138/172
[58] Field of Search ................... 604/282, 96–103, 604/247, 280, 281, 93; 128/D25; 138/103, 118, 172

[56] References Cited

U.S. PATENT DOCUMENTS

| | | | |
|---|---|---|---|
| 1,596,754 | 8/1926 | Moschelle | 604/282 |
| 4,180,076 | 12/1979 | Betancourt | 604/101 |
| 4,553,959 | 11/1985 | Hickey et al. | 604/96 |
| 4,571,241 | 2/1986 | Christopher | 604/282 |
| 4,601,713 | 7/1986 | Fugua | 604/96 |

Primary Examiner—Dalton L. Truluck
Assistant Examiner—Denise Whelton
Attorney, Agent, or Firm—Nies, Webner, Kurz & Bergert

[57] ABSTRACT

A urethral catheter comprising a tube having openings at both ends and at least a portion of the tube having a flexural wall formation permitting compliance of the wall with the urethral shape in use. Longitudinal flexion in the oval-shaped tube is reduced optionally by incorporating a thickened wall portion extending along the catheter about the minor axis thereof, and/or flexural compliance in the lateral direction is reduced optionally by providing a thickened wall portion about the major axis. The catheter is suitable for male patients, and the wall formation can be selected for satisfactory performance under a number of different conditions.

13 Claims, 2 Drawing Sheets

URETHRAL CATHETER

This invention concerns catheters of the kind used for drainage of the bladder via the urethra. Most known forms of urethral catheter consist of a rigid or semi-rigid tube which is inserted into the bladder to effect rapid or controlled drainage thereof, the tube having openings at both ends. Such catheters serve as constant drainage devices wherein the tube remains open and is designed to resist any appreciable degree of collapse or compliance with the shape of the urethra, the latter being non-circular and tending towards a narrow slit.

Another form of the urethral catheter is described in patent specification GB No. 2113554, and consists of a thin-walled preformed tube of a material which will readily approximate in cross-section to the shape of the urethral lumen such that it will undergo substantially complete collapse under normal urethral pressure thus to comply with the irregular and slit-like lumen but permit adequate distension for normal drainage.

Whilst a thin-walled catheter tube of the aforementioned type has the required property of lateral compliance, it has limited resistance to longitudinal flexion. If the tube is bent along its axis as is likely in catheterisation it can kink and thus prevent the passage of urine.

A further difficulty with the thin-walled design is the tendency for the wall to collapse in the prostatic region when used for male catheterisation. In this region it is necessary for the tube to possess a degree of resistance to both lateral collapse and longitudinal bending.

An object of the present invention is to provide a thin-walled urethral catheter having one or more zones of increased flexural resistance for satisfactory performance in certain applications.

According to the present invention there is provided a urethral catheter comprising a tube having openings at both ends, and having in at least a portion of that part of the tube to be situated within the urethra, a flexural wall formation, and at least one zone of increased stiffness extending along said portion such that, according to the intended use, either longitudinal flexion is reduced or flexural compliance in a lateral direction is reduced, or both.

The tube in the aforesaid portion will have a preformed cross-section to which it will return elastically in an unstressed state. If the zone of increased stiffness is formed by increasing the wall thickness there should be substantially no axial or peripheral discontinuity on the inner wall surface of the tube, which should be a smooth approximation to an oval form. The wall is not supported by internal struts or by ridges or grooves, which could decrease the compliance of the catheter when collapsing within the urethra or even prevent its collapse and which could reduce the lumen area available for drainage and provide a wall more likely to encrust and become infected. The reduced lateral compliance and longitudinal flexion is to be provided by increased wall stiffness in certain selected areas.

Examples of uretheral catheters embodying the invention will now be described with reference to the accompanying drawings in which.

Figure 1:
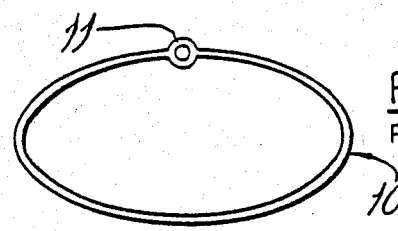
FIG. 1 is a cross-section of a so-called thin-walled catheter having a longitudinal inflation tube for a Foley balloon; as described in GB No. 2113554.

Referring now to the drawings, in FIG. 1 the tube wall generally shown at 10 is produced from a flexural and resilient material which is clinically acceptable and sufficiently durable in use, and is preferably in the region of 0.2 mm thick. Examples of materials from which the tube may be formed are latex, silicone, urethane or poly-vinyl-chloride. As described in GB No. 2113554, the flexural and resilient properties of the tube will permit elastic expansion thereof when normal urethral opening occurs during expulsion of urine through the tube whilst the maximum transmural pressure required to collapse the tube to half of its normal cross-sectional area is in the region of 100 cm water gauge.

A collapsible-walled catheter having these properties will permit substantially normal, or any remaining, sphincter muscle operation in patients suffering from incontinence, and in this way will simulate normal physiological functions as far as possible. This is in direct contrast to the constant drainage function of the more conventional rigid tubed catheter.

Whilst the tube of the kind illustrated in FIG. 1 has the required property of lateral compliance, it has little resistance to longitudinal flexion despite the support afforded by an inflation tube 11 passing along the entire length of the thin-walled tube in the case of a catheter having a retention balloon. The wall of the tube, if bent along its longitudinal axis, will kink and thus prevent or seriously resist the passage of urine.

Referring now to FIGS. 2a to 2d, in accordance with the invention, each tube illustrated includes, over part of its periphery, one or more longitudinally directed zones 12 of increased thickness, tapering to the original thickness at their side edges so that the inner surface retains its smooth elliptical or oval form with no internal projection. Thus, resistance to axial flexion is afforded by the thickened portion. An inflation tube or passage 13 (FIGS. 2a to 2c) is incorporated. The lumen of the catheter tube should have a cross-sectional area sufficient to maintain the required flow passage. Resistance to axial flexion is achieved without a significant increase in lateral compliance when the or each thickened portion is restricted to a section about the minor axis of an elliptical cross-section, as illustrated in FIGS. 2a to 2d.

Figure 2A:
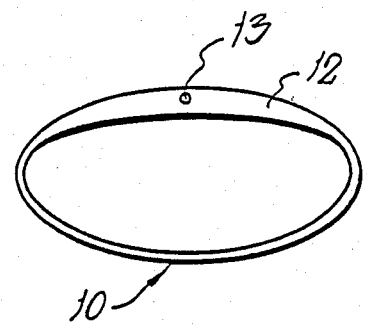
FIGS. 2a to 2d are cross-sections of thin-walled thin-walled catheter tubes each having at least one zone of increased stiffness extending along at least a portion of the length of the tube, in accordance with the invention.
Figure 2B:
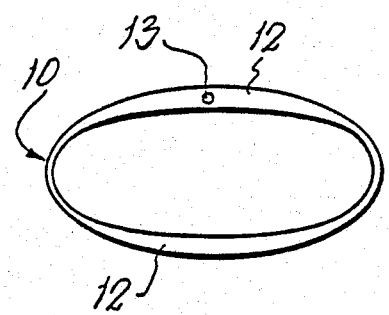
Figure 2C:
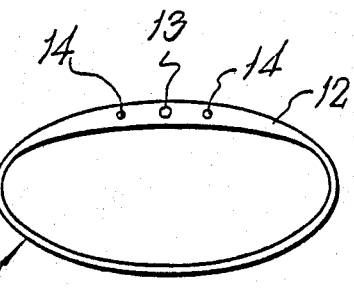

In FIG. 2c, stiffening rods or nylon threads 14 are embedded in a thickened zone 12 to afford further increased stiffness and longitudinal tensile strength.

The thickened zone must however taper smoothly into the thin-walled tube to yield the required properties of compliance. Any rib or groove would provide a discontinuity which would act as a hinge and be a point of increased strain where failure of the material could occur.

Figure 2D:
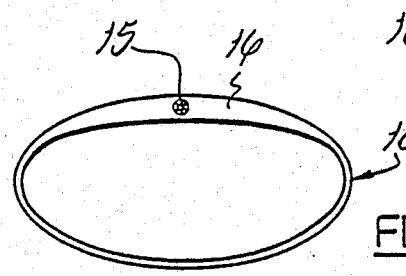

In FIG. 2d, a stiffened inflation tube 15 is embedded in a thickened zone 16 which is of reduced width or azimuthal extent, there being no discontinuity on the internal wall surface, with a smooth transition between zone 16 and the remainder of the wall. It is clear therefore that the zone of increased flexural resistance can be provided by increasing the thickness of the wall and/or its inherent stiffness, and this may be supplemented if necessary by the inclusion of fibres, strips or rods of a more rigid material.

The zone or zones of increased stiffness should be of limited azimuthal extent. Each zone should be less than one quarter of the overall periphery. When more than one zone is included the thickened wall zones in adjacent areas may combine to form a section of increased azimuthal extent. The total azimuthal extent of the thickened zones in the tube should be limited to less than three-fourths of the overall periphery.

The wall features which provide for increased resistance to axial flexion while retaining the lateral compliance are most simply described with reference to a non-circular or oval tube cross-section. Catheter tubes of oval cross-section, as is preferable in order to comply with the similarly shaped lumen of the urethra, are shown in the drawings. To provide resistance to longitudinal flexion with little reduction in lateral compliance, the thickened portions of the wall should be restricted to the regions about the minor axis as illustrated in FIGS. 2a to 2d. The essential requirement is that the moment of inertia, or the effective modulus of the wall, is increased by increasing the wall thickness, or modulus, at positions of minimum wall curvature in the transverse plane. Lateral compliance in an oval tube is reduced only slightly if the wall is thickened in these positions.

Notwithstanding the increased longitudinal stiffness, the overall lateral compliance of the tubes illustrated in FIGS. 2a to 2d should be such that the maximum transmural pressure required to collapse the tube to one half of its normal external cross-sectional area is 100 centimeters water gauge.

A catheter whose tube is permitted to be fully collapsed cannot, however, be used throughout the entire urethra of a male patient with prostatic enlargement or stricture. Such patients suffer from retention of urine rather than incontinence, and it is necessary to provide for them a catheter section which will remain partially open under external pressure whilst producing minimum distension and pressure on the urethra where it passes through the prostatic region, in which it assumes a tortuous path. Thus, the catheter tube must be capable of accommodating the required drainage of urine. The extent of lateral flexural compliance must be reduced with respect to those illustrated in FIGS. 2a to 2d.

To convert a thin-walled tube to one which will collapse to a limited extent it is necessary to increase the resistance of the wall to flexion in the transverse plane. Lateral compliance is thus minimised by thickening or stiffening the wall about the area of maximum curvature. Such thickening should taper into the thin-walled sections of the tube leaving a smooth internal wall surface without discontinuity. The thickening decreases the lateral compliance by increasing the resistance of the wall to flexion but does not provide ridges, extensions or other projections into the lumen of the tube, since such projections would reduce the area available for drainage and tend to encrust at the points of engagement, preventing expansion of the tube and thus leading to bypassing of urine. The thickened section, if the tube is of generally ellipitcal shape, is in zones 17 which lie about the major axis of the ellipse as illustrated in FIGS. 3a to 3c.

Figure 3A:
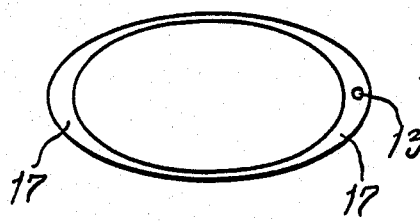
FIGS. 3a to 3c are further cross-sections of thin-walled catheter tubes each having at least one zone of increased stiffness extending along at least a portion of the length of the tube.

An inflation tube or passage 13 can be incorporated in one of the thickened zones 17 at or close to the major axis as in FIG. 3a. Alternatively the zones 17 at or close to the major axis can be joined to extend throughout one major side and incorporate the tube in this position at or close to the minor axis as in FIGS. 3b and 3c. In FIG. 3c the outer wall surface is preformed to conform more closely to the natural shape of the urethral lumen, whilst the inner wall surface is entirely smooth.

Figure 3B:
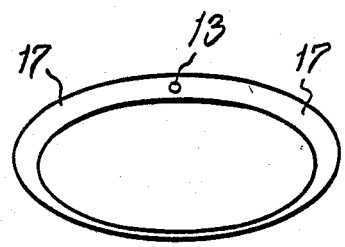
Figure 3C:
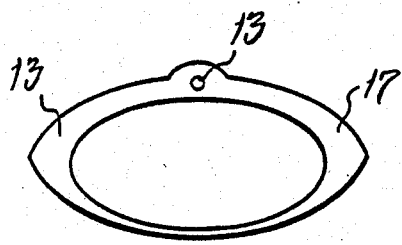
Figure 4A:
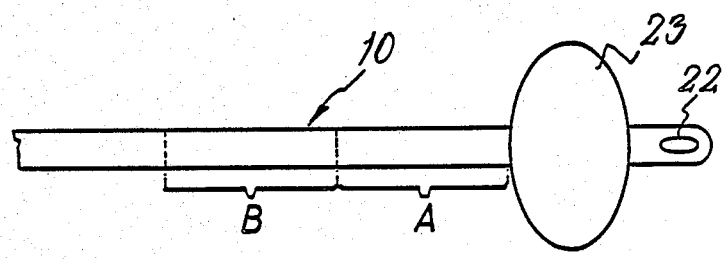
FIGS. 4a and 4b are partial views of catheters embodying the invention and usable for male and female patients respectively.

FIG. 4a illustrates an example of a male catheter having an inlet 22 at its inner end and a Foley retention balloon 23 behind which is a first section A of limited lateral compliance, with an inflation tube, typically as shown in FIGS. 3a to 3c. This is followed by a section B which may be of the form illustrated in any of FIGS. 2a to 2d, or, if longitudinal flexion is permitted, the type illustrated in FIG. 1. The remainder of the catheter, which will be situated outside the urethra in use, can be of a conventional rigid type.

Figure 4B:
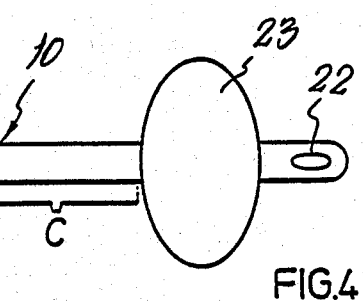

A catheter of the type illustrated in FIG. 4b is suitable for female patients and consists of a shorter internal section illustrated at C which can be of the compliant form as illustrated in FIGS. 2a to 2d or of the kind having reduced lateral compliance as illustrated in FIGS. 3a to 3c.

I claim:

1. A urethral catheter comprising a tube having openings at both ends, and having in at least a portion of the length of the tube to be situated within the urethra, a thin flexible wall having a smooth inner surface of elliptical or oval form in cross-section such that, in said portion, the wall will undergo substantially complete collapse under normal urethral pressure, characterized by at least one zone of increased wall thickness extending around a selected part of the cross-sectional periphery of the tube and extending longitudinally in said portion to prevent the wall from collapsing completely other than by normal urethral pressure or from folding longitudinally, according to the part selected and wherein said thin flexible wall portion of said tube outside said zone of increased wall thickness has flexural and resilient properties which permit elastic expansion of the tube wall when normal urethral opening occurs during expulsion of urine through the tube, with said thin flexible wall portion being formed of a material having a lateral compliance such that the maximum transmural pressure required to collapse a tube formed entirely of such material to half its normal cross-sectional area would be 100 cm water guage.

2. A urethral catheter according to claim 1, wherein the cross-sectional periphery of said tube is generally oval thus having major and minor axes at right-angles, said zone of increased wall thickness extending about said minor axis in a region of minimum curvature.

3. A urethral catheter according to claim 2, including two oppositely disposed zones of increased wall thickness extending about the minor axis of the tube wall.

4. A urethral catheter according to claim 2, including an inflation tube or passage extending within said thickened wall zone.

5. A urethral catheter according to claim 1 including at least one stiffening rod extending longitudinally of the tube within said zone of increased wall thickness.

6. A urethral catheter according to claim 2, wherein a reinforced inflation tube extends longitudinally throughout said zone of increased wall thickness.

7. A urethral catheter according to claim 1, wherein said tube is of generally oval shape thus having major and minor axes at right angles, said zone of increased wall thickness extending about said major axis in a region of maximum curvature.

8. A urethral catheter according to claim 7, including a pair of thickened wall zones extending about said major axis, one of which includes an inflation tube or passage extending along the wall.

9. A urethral catheter according to claim 8, wherein said pair of thickened wall zones are joined between two corresponding ends thereof to extend about the minor axis of the tube, there being an inflation tube or passage extending through said thickened wall zone on or close to the minor axis.

10. A urethral catheter according to claim 1, wherein the outer wall surface is pre-formed to conform closely to the natural shape of the urethral lumen.

11. A urethral catheter according to claim 1, in which the inner wall surface of the tube has a continuous curvature, there being a smooth transition between the or each thickened wall zone and the remainder of the tube wall.

12. A urethral catheter according to claim 1, comprising a first portion of the length of the tube close to one end of the catheter to be introduced first into the urethra, in which at least one zone of increased wall thickness is provided to prevent the wall from collapsing other than by normal urethral pressure, and a second portion longitudinally outwardly of said first portion and aligned therewith, including at least one zone of increased wall thickness to prevent the wall from folding longitudinally in said second portion.

13. A urethral catheter according to claim 12, including a Foley balloon surrounding the tube adjacent to the innermost end of said first portion.

* * * * *